(12) United States Patent
Rupp et al.

(10) Patent No.: US 12,426,936 B2
(45) Date of Patent: *Sep. 30, 2025

(54) ULTRASONIC AND RADIOFREQUENCY ENERGY PRODUCTION AND CONTROL FROM A SINGLE POWER CONVERTER

(71) Applicant: Covidien LP, Mansfield, MA (US)

(72) Inventors: Steven C. Rupp, Arvada, CO (US); Robert B. Smith, Loveland, CO (US); Daniel A. Friedrichs, Aurora, CO (US)

(73) Assignee: Covidien LP, Mansfield, MA (US)

( * ) Notice: Subject to any disclaimer, the term of this patent is extended or adjusted under 35 U.S.C. 154(b) by 189 days.

This patent is subject to a terminal disclaimer.

(21) Appl. No.: 17/322,030

(22) Filed: May 17, 2021

(65) Prior Publication Data

US 2021/0267659 A1 Sep. 2, 2021

Related U.S. Application Data

(63) Continuation of application No. 15/231,890, filed on Aug. 9, 2016, now Pat. No. 11,006,997.

(51) Int. Cl.
*A61B 18/12* (2006.01)
*A61B 17/00* (2006.01)
(Continued)

(52) U.S. Cl.
CPC .. *A61B 18/1206* (2013.01); *A61B 17/320068* (2013.01); *A61B 17/320092* (2013.01); *A61B 18/1442* (2013.01); *A61N 7/00* (2013.01); *B06B 3/00* (2013.01); *A61B 2017/00154* (2013.01); *A61B 2017/00477* (2013.01);
(Continued)

(58) Field of Classification Search
CPC ........ A61B 18/1206; A61B 17/320068; A61B 17/320092; A61B 18/1442; A61B 2017/00154; A61B 2017/00477; A61B 2018/00577; A61B 2018/00589; A61B 2018/00601; A61B 2018/0063; A61B 2018/00779; A61B 2018/00827; A61B 2018/00892; A61B 2018/00994;
(Continued)

(56) References Cited

U.S. PATENT DOCUMENTS 3,252,052 A 5/1966 Nash
3,514,689 A 5/1970 Giannamore
(Continued)

FOREIGN PATENT DOCUMENTS

CN 1494931 A 5/2004
CN 203483460 U 3/2014
(Continued)

OTHER PUBLICATIONS

Sugita et al., "Bipolar Coagulator with Automatic Thermocontrol" J. Neurosurg., vol. 41, Dec. 1944, pp. 777-779.
(Continued)

*Primary Examiner* — Ronald Hupczey, Jr.

(57) ABSTRACT

A generator is configured to output two or more waveforms at different frequencies. In particular, the generator is configured to provide an ultrasonic waveform, which may be suitable for driving a transducer of an ultrasonic surgical instrument, and electrosurgical radiofrequency energy, which may be suitable for electrosurgical instruments.

18 Claims, 4 Drawing Sheets

(51) Int. Cl.
  *A61B 17/32* (2006.01)
  *A61B 18/00* (2006.01)
  *A61B 18/14* (2006.01)
  *A61B 90/00* (2016.01)
  *A61N 7/00* (2006.01)
  *B06B 3/00* (2006.01)

(52) U.S. Cl.
  CPC ............... *A61B 2018/00577* (2013.01); *A61B 2018/00589* (2013.01); *A61B 2018/00601* (2013.01); *A61B 2018/0063* (2013.01); *A61B 2018/00779* (2013.01); *A61B 2018/00827* (2013.01); *A61B 2018/00892* (2013.01); *A61B 2018/00994* (2013.01); *A61B 2018/124* (2013.01); *A61B 2018/126* (2013.01); *A61B 2090/065* (2016.02)

(58) Field of Classification Search
  CPC ........ A61B 2018/124; A61B 2018/126; A61N 7/00; B06B 3/00
  See application file for complete search history.

(56) References Cited

U.S. PATENT DOCUMENTS

| | | | |
|---|---|---|---|
| 3,551,786 A | 12/1970 | Gulik | |
| 3,641,422 A | 2/1972 | Farnsworth et al. | |
| 3,801,800 A | 4/1974 | Newton | |
| 3,826,263 A | 7/1974 | Cage et al. | |
| 3,885,569 A | 5/1975 | Judson | |
| 3,897,787 A | 8/1975 | Ikuno et al. | |
| 3,978,393 A | 8/1976 | Wisner et al. | |
| 4,102,341 A | 7/1978 | Ikuno et al. | |
| 4,247,815 A | 1/1981 | Larsen et al. | |
| 4,287,557 A | 9/1981 | Brehse | |
| 4,378,801 A | 4/1983 | Oosten | |
| 4,416,276 A | 11/1983 | Newton et al. | |
| 4,416,277 A | 11/1983 | Newton et al. | |
| 4,436,091 A | 3/1984 | Banko | |
| 4,438,766 A | 3/1984 | Bowers | |
| 4,559,943 A | 12/1985 | Bowers | |
| 4,569,345 A | 2/1986 | Manes | |
| 4,572,190 A | 2/1986 | Azam et al. | |
| 4,590,934 A | 5/1986 | Malis et al. | |
| 4,630,218 A | 12/1986 | Hurley | |
| 4,644,955 A | 2/1987 | Mioduski | |
| 4,658,815 A | 4/1987 | Farin et al. | |
| 4,658,819 A | 4/1987 | Harris et al. | |
| 4,658,820 A | 4/1987 | Klicek | |
| 4,691,703 A | 9/1987 | Auth et al. | |
| 4,716,897 A * | 1/1988 | Noguchi | A61B 18/12 606/34 |
| 4,739,759 A | 4/1988 | Rexroth et al. | |
| 4,754,757 A | 7/1988 | Feucht | |
| 4,767,999 A | 8/1988 | VerPlanck | |
| 4,860,745 A | 8/1989 | Farin et al. | |
| 4,887,199 A | 12/1989 | Whittle | |
| 4,959,606 A | 9/1990 | Forge | |
| 5,024,668 A | 6/1991 | Peters et al. | |
| 5,113,116 A | 5/1992 | Wilson | |
| 5,160,334 A * | 11/1992 | Billings | A61B 18/14 606/49 |
| 5,304,917 A | 4/1994 | Somerville | |
| 5,325,073 A | 6/1994 | Hasegawa | |
| 5,334,183 A | 8/1994 | Wuchinich | |
| 5,341,807 A | 8/1994 | Nardella | |
| 5,370,672 A | 12/1994 | Fowler et al. | |
| 5,438,302 A | 8/1995 | Goble | |
| 5,472,443 A | 12/1995 | Cordis et al. | |
| 5,500,616 A | 3/1996 | Ochi | |
| 5,531,774 A | 7/1996 | Schulman et al. | |
| 5,540,684 A | 7/1996 | Hassler, Jr. | |
| 5,558,671 A | 9/1996 | Yates | |
| 5,559,688 A | 9/1996 | Pringle | |
| 5,596,466 A | 1/1997 | Ochi | |
| 5,628,771 A | 5/1997 | Mizukawa et al. | |
| 5,658,322 A | 8/1997 | Fleming | |
| 5,674,217 A | 10/1997 | Wahlstrom et al. | |
| 5,694,304 A | 12/1997 | Telefus et al. | |
| 5,712,772 A | 1/1998 | Telefus et al. | |
| 5,817,093 A | 10/1998 | Williamson, IV et al. | |
| 5,871,481 A | 2/1999 | Kannenberg et al. | |
| 6,017,354 A | 1/2000 | Culp et al. | |
| 6,044,283 A | 3/2000 | Fein et al. | |
| 6,063,075 A | 5/2000 | Mihori | |
| 6,090,123 A | 7/2000 | Culp et al. | |
| 6,142,992 A | 11/2000 | Cheng et al. | |
| 6,162,217 A | 12/2000 | Kannenberg et al. | |
| 6,188,211 B1 | 2/2001 | Rincon-Mora et al. | |
| 6,235,020 B1 | 5/2001 | Cheng et al. | |
| 6,296,636 B1 | 10/2001 | Cheng et al. | |
| 6,329,778 B1 | 12/2001 | Culp et al. | |
| 6,629,974 B2 | 10/2003 | Penny et al. | |
| 6,723,091 B2 | 4/2004 | Goble et al. | |
| 6,740,079 B1 | 5/2004 | Eggers et al. | |
| 6,923,804 B2 | 8/2005 | Eggers et al. | |
| 6,966,907 B2 | 11/2005 | Goble | |
| 6,975,087 B1 * | 12/2005 | Crabill | G05B 11/42 318/590 |
| 7,004,174 B2 | 2/2006 | Eggers et al. | |
| 7,058,372 B1 | 6/2006 | Pardoen et al. | |
| 7,190,933 B2 | 3/2007 | De Ruijter et al. | |
| 7,244,255 B2 | 7/2007 | Daners et al. | |
| 7,364,972 B2 | 4/2008 | Ono et al. | |
| D574,323 S | 8/2008 | Waaler | |
| 7,422,582 B2 | 9/2008 | Malackowski et al. | |
| 7,517,351 B2 | 4/2009 | Culp et al. | |
| 7,525,398 B2 | 4/2009 | Nishimura et al. | |
| 7,722,603 B2 | 5/2010 | McPherson | |
| 7,863,841 B2 | 1/2011 | Menegoli et al. | |
| 7,927,328 B2 | 4/2011 | Orszulak et al. | |
| 9,028,479 B2 | 5/2015 | Orszulak | |
| 2003/0181898 A1 | 9/2003 | Bowers | |
| 2005/0203504 A1 | 9/2005 | Wham et al. | |
| 2007/0129716 A1 | 6/2007 | Daw et al. | |
| 2007/0173804 A1 | 7/2007 | Wham et al. | |
| 2007/0173806 A1 | 7/2007 | Orszulak et al. | |
| 2008/0125768 A1 * | 5/2008 | Tahara | A61B 18/1206 606/34 |
| 2009/0248003 A1 | 10/2009 | Orszulak | |
| 2010/0063494 A1 | 3/2010 | Orszulak | |
| 2010/0168742 A1 | 7/2010 | Shibata | |
| 2011/0087213 A1 | 4/2011 | Messerly et al. | |
| 2011/0087256 A1 | 4/2011 | Wiener et al. | |
| 2011/0115562 A1 | 5/2011 | Gilbert | |
| 2011/0178516 A1 | 7/2011 | Orszulak et al. | |
| 2011/0319881 A1 | 12/2011 | Johnston | |
| 2012/0059286 A1 | 3/2012 | Hastings et al. | |
| 2012/0078139 A1 | 3/2012 | Aldridge | |
| 2012/0215216 A1 | 8/2012 | Friedrichs et al. | |
| 2013/0035679 A1 * | 2/2013 | Orszulak | A61B 18/1445 330/69 |
| 2013/0331874 A1 * | 12/2013 | Ross | A61B 17/320092 702/19 |
| 2014/0180274 A1 * | 6/2014 | Kabaya | A61B 18/1206 606/34 |
| 2014/0276754 A1 * | 9/2014 | Gilbert | A61B 18/1206 606/33 |
| 2015/0025523 A1 | 1/2015 | Friedrichs et al. | |
| 2015/0238248 A1 | 8/2015 | Thompson et al. | |
| 2017/0086910 A1 * | 3/2017 | Wiener | A61B 18/1445 |

FOREIGN PATENT DOCUMENTS

| | | |
|---|---|---|
| DE | 179607 C | 11/1906 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |

(56) References Cited

FOREIGN PATENT DOCUMENTS

| | | |
|---|---|---|
| DE | 2407559 A1 | 8/1975 |
| DE | 2602517 A1 | 7/1976 |
| DE | 2504280 A1 | 8/1976 |
| DE | 254968 A | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0424687 A1 | 5/1991 |
| EP | 0556705 A1 | 8/1993 |
| EP | 0608609 A2 | 8/1994 |
| EP | 0694291 A1 | 1/1996 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1151725 A1 | 11/2001 |
| EP | 1366724 A1 | 12/2003 |
| EP | 1366725 A1 | 12/2003 |
| EP | 1500378 A1 | 1/2005 |
| EP | 1681026 A2 | 7/2006 |
| EP | 1776929 A1 | 4/2007 |
| EP | 1810632 A1 | 7/2007 |
| EP | 2025297 A2 | 2/2009 |
| EP | 2100566 A1 | 9/2009 |
| EP | 2469699 A2 | 6/2012 |
| EP | 2674118 A2 | 12/2013 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| GB | 702510 A | 1/1954 |
| GB | 1290304 A | 9/1972 |
| GB | 2434872 A | 8/2007 |
| GB | 2521228 A | 6/2015 |
| JP | 63005876 | 1/1988 |
| JP | 2002065690 A | 3/2002 |
| JP | 2005185657 A | 7/2005 |
| JP | 2008279254 A | 11/2008 |
| JP | 2009240780 A | 10/2009 |
| JP | 2011109663 A | 6/2011 |
| SU | 166452 | 11/1964 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2004/078050 A2 | 9/2004 |
| WO | 2006050888 A1 | 5/2006 |
| WO | 2007067522 A2 | 6/2007 |
| WO | 2008043999 A2 | 4/2008 |
| WO | 2008053532 A1 | 5/2008 |
| WO | 2008135736 A1 | 11/2008 |
| WO | 2011008672 A2 | 1/2011 |
| WO | 2016091401 A1 | 6/2016 |

OTHER PUBLICATIONS

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Anderson et al., "A Numerical Study of Rapid Heating for High Temperature Radio Frequency Hyperthermia" International Journal of Bio-Medical Computing, 35 (1994) pp. 297-307.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Wald et al., "Accidental Burns", JAMA, Aug. 16, 1971, vol. 217, No. 7, pp. 916-921.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic Computerized Bipolar Coagulator" Journal of Neurosurgery 75:1, (Jul. 1991) pp. 148-151.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15: (1984) pp. 945-950.

Ogden Goertzel Alternative to the Fourier Transform: Jun. 1993 pp. 485-487 Electronics World; Reed Business Publishing, Sutton, Surrey, BG vol. 99, No. 9. 1687.

Valleylab Brochure "Valleylab Electroshield Monitoring System" 2 pp. Nov. 1995.

Vallfors et al., "Automatically Controlled Bipolar Electrosoagulation-'COA-COMP'" Neurosurgical Review 7:2-3 (Jun. 1984) pp. 187-190.

Richard Wolf Medical Instruments Corp. Brochure, "Kleppinger Bipolar Forceps & Bipolar Generator" 3 pp. Jan. 1989.

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

Prutchi et al. "Design and Development of Medical Electronic Instrumentation", John Wiley & Sons, Inc. Feb. 2005.

Muller et al. "Extended Left Hemicolectomy Using the LigaSure Vessel Sealing System" Innovations That Work; Company Newsletter; Sep. 1999.

Medtrex Brochure—Total Control at Full Speed, "The O.R. Pro 300" 1 p. Sep. 1998.

Geddes et al., "The Measurement of Physiologic Events by Electrical Impedence" Am. J. MI, Jan. Mar. 1964, pp. 16-27.

Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Extended European Search Report issued in Appl. No. EP 17185396.3 dated Jan. 8, 2018 (8 pages).
Chinese Office Action dated Oct. 9, 2019 issued in corresponding CN Appln. No. 201710644219.9.
Chinese Office Action dated Oct. 9, 2019 issued in corresponding CN Appln. No. 201710644219.9. (Summary only).
The European Examination Report dated Jul. 9, 2021 issued in corresponding EP Appln. No. 17185396.3.
Office Action issued in corresponding Chinese Application No. 202110568610.1 dated Jan. 25, 2024, together with English Language translation, machine Translated with DeepL.com (free version).

* cited by examiner

ULTRASONIC AND RADIOFREQUENCY ENERGY PRODUCTION AND CONTROL FROM A SINGLE POWER CONVERTER

CROSS-REFERENCE TO RELATED APPLICATIONS

This application is a continuation of U.S. patent application Ser. No. 15/231,890, filed Aug. 9, 2016, now U.S. Pat. No. 11,006,997. The entire contents of the above application is hereby incorporated by reference.

BACKGROUND

Technical Field

The present disclosure relates to systems and methods for powering surgical energy devices at multiple frequencies. In particular, the present disclosure relates to a single generator configured to power one or more outputs at specified frequencies and regulated amplitude suitable for powering a first device at a first frequency and a second device at a second frequency, which is different from the first frequency. Specifically, the present disclosure provides for a single power source capable of energizing an ultrasonic device and an electrosurgical device.

Background of Related Art

Electrosurgery involves application of high radio frequency ("RF") electrical current to a surgical site to cut, ablate, desiccate, or coagulate tissue. In monopolar electrosurgery, a source or active electrode delivers radio frequency alternating current from the RF generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like.

Ultrasonic surgical devices have also been demonstrated to provide hemostasis and efficient dissection of tissue with minimum lateral thermal damage and low smoke generation. Unlike electrosurgical devices, which require electrical current to flow through a patient, ultrasonic surgical devices operate by applying mechanical motion through an ultrasonic probe using an ultrasonic transducer that is driven at a resonant frequency.

Each of the electrosurgical and ultrasonic devices has their desired uses due to their inherent operational characteristics. Accordingly, there is a need for a system and a generator configured to operate both types of the instruments to provide for new and improved surgical techniques and applications.

SUMMARY

The present disclosure provides a surgical generator configured to output two or more waveforms at different frequencies allowing the surgical generator to provide low-frequency output, which may be suitable for driving an ultrasonic transducer of an ultrasonic surgical instrument, and a high-frequency output, which may be suitable for an electrosurgical instrument.

According to an embodiment of the present disclosure a surgical generator is provided. The surgical generator includes a power supply, an amplifier coupled to the power supply and configured to output a first waveform and a second waveform, and a controller coupled to the amplifier. The controller is configured to provide at least one of a first control signal and a second control signal to the amplifier. The controller includes a first controller configured to provide the first control signal to the amplifier to generate the first waveform and a second controller configured to provide the second control signal to the amplifier to generate the second waveform. The controller further includes a switch configured to select at least one of the first control signal and the second control signal.

According to another embodiment of the present disclosure, a surgical system is provided. The system includes a surgical generator, a first instrument, and a second instrument. The surgical generator includes a power supply, an amplifier coupled to the power supply and configured to output a first waveform and a second waveform, a controller coupled to the amplifier, a first output, and a second output. The controller is configured to provide at least one of a first control signal and a second control signal to the amplifier. The controller includes a first controller configured to provide the first control signal to the amplifier to generate the first waveform and a second controller configured to provide the second control signal to the amplifier to generate the second waveform. The controller further includes a switch configured to select at least one of the first control signal and the second control signal. The first output outputs the first waveform controlled by the first control signal and the second output outputs the second waveform controller by the second control signal. The first instrument is coupled to the first output and energizable by the first waveform, and the second instrument is coupled to the second output and energizable by the second waveform.

According to an aspect of the above-described embodiment, the first instrument is an ultrasonic instrument including a transducer energizable by the first waveform and the second instrument is an electrosurgical instrument including at least one electrode configured to contact tissue and transmit the second waveform thereto.

According to one aspect of the above-described embodiment, the first instrument is a first electrosurgical instrument including at least one first electrode configured to contact tissue and transmit the first waveform thereto and the second instrument is a second electrosurgical instrument including at least second one electrode configured to contact tissue and transmit the second waveform thereto.

According to an aspect of any of the above-described embodiments, the first controller is an electrosurgical controller and the first control signal is an RF control signal, and the second controller is an ultrasonic controller and the second control signal is an ultrasonic control signal.

According to an aspect of any of the above-described embodiments, the ultrasonic controller includes a motional bridge, a proportional-integral-derivative controller, a pulse-width modulator, a frequency control unit, and a signal generator. The motional bridge is configured to receive an output current of the amplifier and generate a motional feedback signal in proportion to and in phase with the mechanical motion of an ultrasonic transducer. The proportional-integral-derivative controller is configured to correct the motional feedback signal based on a comparison of the motional feedback signal and a desired displacement of the ultrasonic transducer. The pulse-width modulator is configured to modulate the second control signal. The frequency control unit is configured to receive an output current of the amplifier and generate a frequency control signal based on a comparison of the frequency of the second waveform and a resonant frequency of the ultrasonic transducer. The signal generator is configured to generate the ultrasonic control signal based on the motional feedback signal and the frequency control signal.

According to an aspect of any of the above-described embodiments, the controller includes a processor and a memory. In an embodiment, the amplifier is a non-resonant amplifier and is coupled to an active terminal and a return terminal which are coupled to a plurality of ports. In yet another embodiment, the surgical generator further comprises a hub, wherein the hub is coupled to the active and returns terminals and the plurality of ports. The hub selectively couples each of the plurality of ports to the active terminal and return terminal. According to another embodiment, the surgical generator further comprises at least one of a current sensor, a voltage sensor, and a power sensor.

BRIEF DESCRIPTION OF THE DRAWINGS

The present disclosure may be understood by reference to the accompanying drawings, when considered in conjunction with the subsequent, detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

A generator according to the present disclosure can operate with ultrasonic and electrosurgical instruments at multiple frequencies. In particular, the generator may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator includes electronic circuitry configured to generate an ultrasonic waveform suitable for driving ultrasonic transducers of ultrasonic instruments and radio frequency energy specifically suited for powering electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
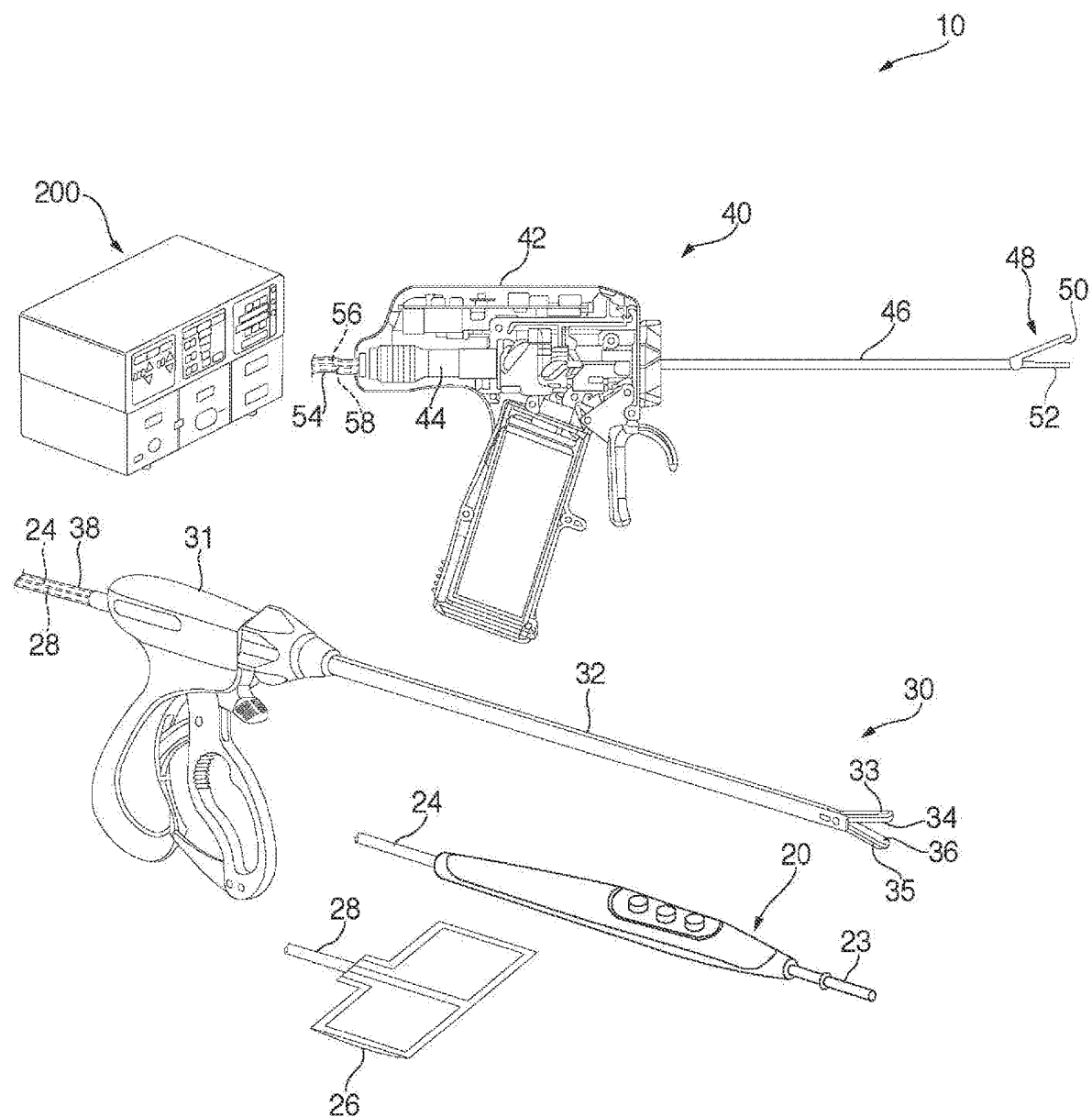
FIG. 1 is a perspective view of a surgical system according to an embodiment of the present disclosure.

FIG. 1 is a perspective view of the components of one illustrative embodiment of a dual-output system 10 according to the present disclosure. The system 10 may include one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 230 (FIG. 3) of the generator 200, allowing the instrument 20 to cut, coagulate, thermally or non-thermally ablate and/or otherwise treat tissue. The alternating current is returned to the generator 200 through a return electrode pad 26 via a return line 28 at a return terminal 232 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
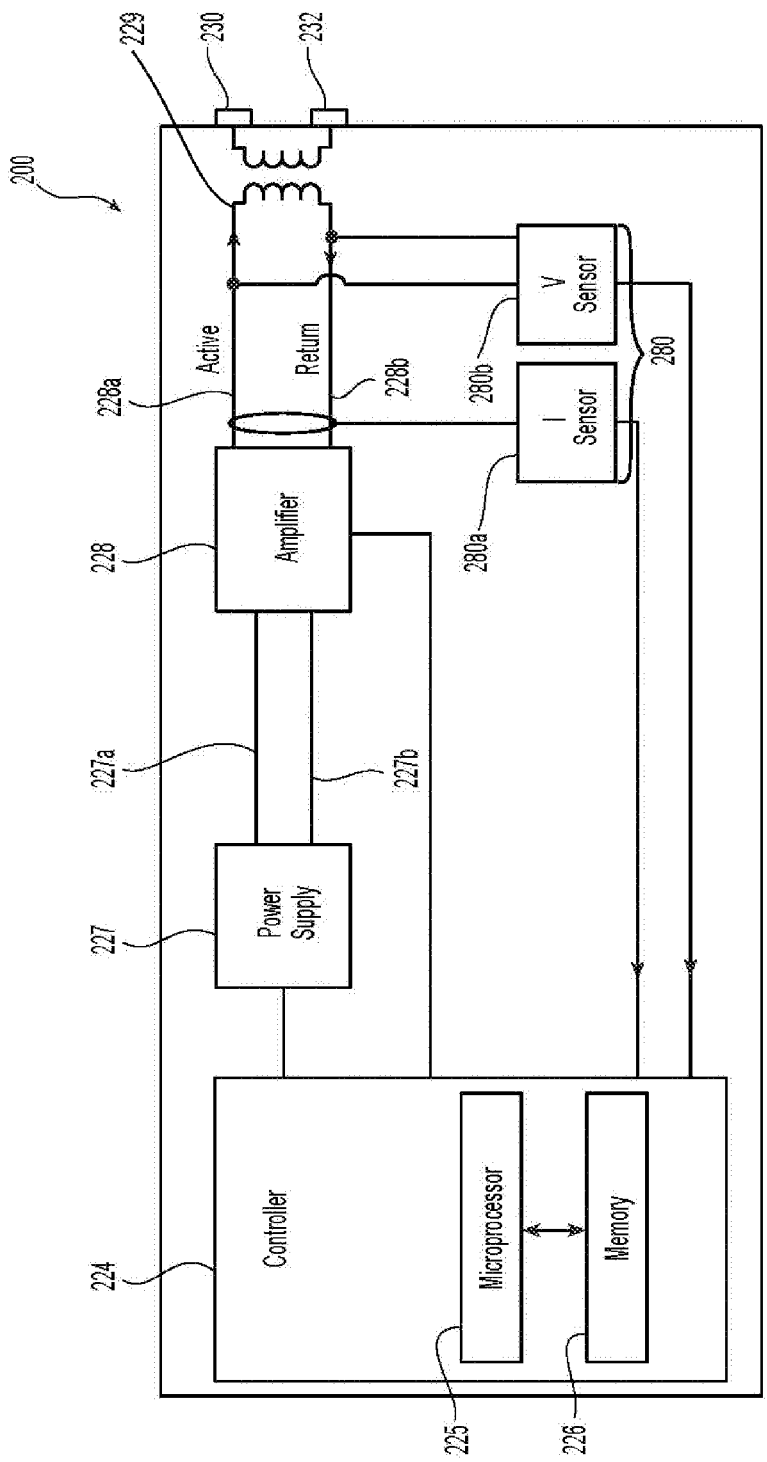
FIG. 3 is a schematic, block diagram of the generator of FIG. 1.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 230, 232, respectively (FIG. 3). The electrosurgical forceps 30 is coupled to the generator 200 at a port having connections to the active and return terminals 230 and 232 (e.g., pins) via a plug disposed at the end of the cable 38, wherein the plug includes contacts from the supply and return lines 24, 28 as described in more detail below.

The system 10 also includes an ultrasonic surgical instrument 40, which includes a housing 42 having an ultrasonic transducer 44 disposed therein. The ultrasonic surgical instrument 40 also includes a waveguide 46 having an end effector 48 disposed at a distal end thereof. The distal end effector 48 includes a movable jaw member 50 and a probe 52. The ultrasonic transducer 44 is connected to the generator 200 via a cable 54 that includes supply lines 56 and 58 coupled to active and return terminals 230 and 232 (FIG. 3), respectively. The ultrasonic probe 52 is coupled to the ultrasonic transducer 44, such that when the ultrasonic transducer 44 is actuated in response to an ultrasonic waveform from the generator 200, the ultrasonic transducer 44 generates ultrasonic mechanical motion within the probe 52, which may be used to seal and/or cut tissue.

Figure 2:
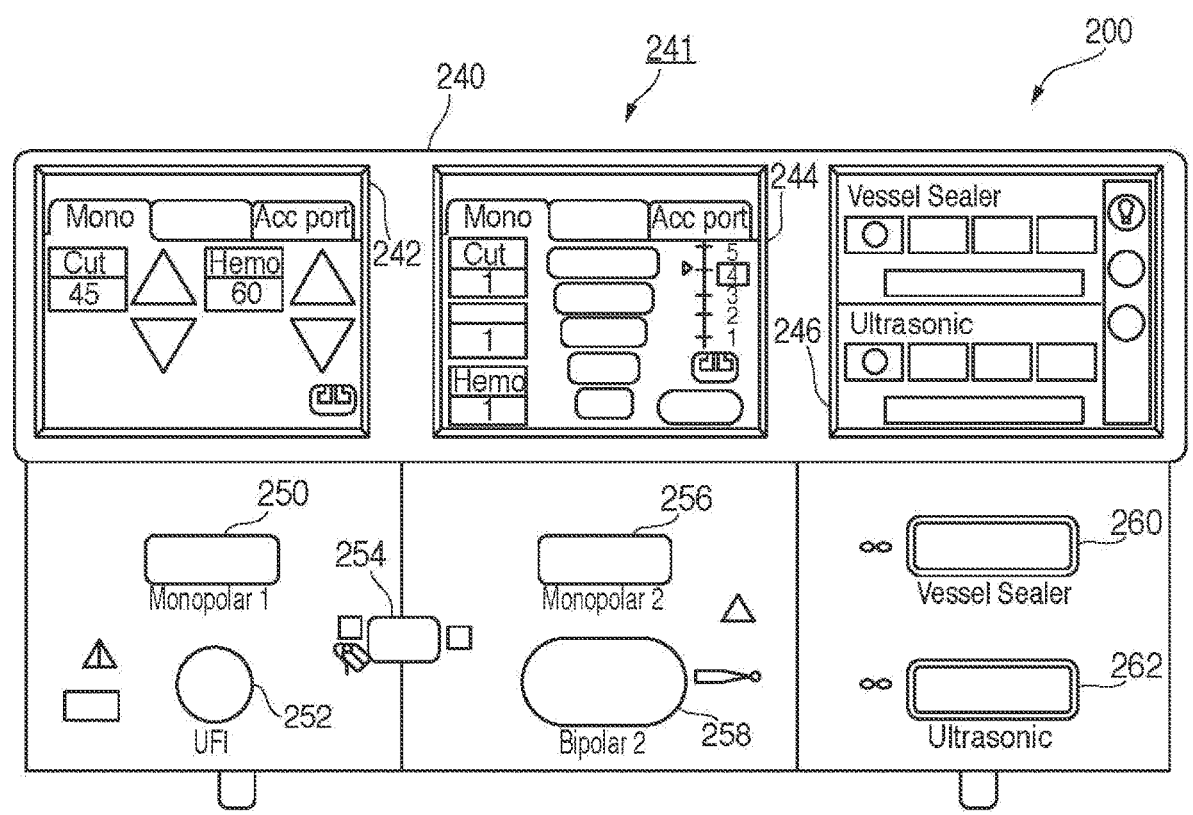
FIG. 2 is a front view of a dual-output generator of FIG. 1.

With reference to FIG. 2, a front face 240 of the generator 200 is shown. The generator 200 may include a plurality of ports 250-262 to accommodate various types of surgical instruments (e.g., monopolar electrosurgical instrument 20, electrosurgical forceps 30, ultrasonic surgical instrument 40, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user then adjusts inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional inputs (e.g., replicating inputs of the generator 200). Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 and the ultrasonic surgical instrument 40 that may be plugged into the ports 260 and 262, respectively. The generator 200 outputs energy through the port 260 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to the controller 224 where the setting may be saved in memory 226. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30.

The active and return terminals 230 and 232 are coupled to ports 250-262 through a hub or switch (not shown). As described in further detail below, the hub or switch couples active and return terminals 230 and 232 to ports 250-262 depending on what instrument is coupled to the generator and the desired output energy (i.e. ultrasonic or radiofrequency energy)

FIG. 3 shows a schematic block diagram of the generator 200 configured to output both ultrasonic ("US") energy and radiofrequency ("RF") energy. In particular, the generator 200 is capable of outputting a low-frequency waveform to the transducer 44 (FIG. 1) of the ultrasonic surgical instrument 40 and a high-frequency waveform to the monopolar electrosurgical instrument 20 and/or electrosurgical forceps 30. In embodiments, the generator 200 may also configured to simultaneously output low-frequency energy for energizing any suitable electrosurgical instrument and output high-frequency energy for energizing another electrosurgical instrument.

The generator 200 includes a controller 224, a power supply 227, and an amplifier 228. The power supply 227 may be a high voltage, DC power supply connected to an AC source and provides high voltage, DC power to amplifier 228 via leads 227a and 227b, which then converts high voltage, DC power into treatment energy (e.g., electrosurgical or ultrasonic) and delivers the energy to the active terminal 230. The energy is returned thereto via the return terminal 232. Active terminal 230 and return terminal 232 are coupled to a hub (not shown) which in turn is coupled to the plurality of ports 250-262 of the generator 200. For example, an ultrasonic waveform suitable for driving a transducer 44 of an ultrasonic instrument 40 is delivered through port 262, or electrosurgical RF energy for energizing the monopolar electrosurgical instrument 20 and/or electrosurgical forceps 30 may be delivered through ports 256 and 258, respectively. The active terminal 230 and return terminal 232 are coupled to the amplifier 228 through an isolation transformer 229. The amplifier 228 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Amplifier 228 is a non-resonant amplifier capable of operating over a wide range of frequencies from about 50 kHz to 2 MHz. A non-resonant amplifier, as used herein, denotes an amplifier lacking any tuning components intended to establish a fixed operating frequency, i.e., inductors, capacitors, etc. The amplifier 228 includes transistor drive circuits capable of spanning different switching time periods required to operate over the wide range of frequencies. The amplifier 228 also includes switching elements (e.g. transistors and diodes) capable of withstanding peak currents and voltages which vary significantly between the different modes.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or amplifier 228 allowing the processor 225 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or amplifier 228, which adjusts the DC and/or power supply, respectively. Those skilled in the art will appreciate that the processor 225 may be substituted for by using any logic processor (e.g., control circuit) adapted to perform the calculations and/or set of instructions described herein including, but not limited to, field programmable gate array, digital signal processor, and combinations thereof.

The generator 200 according to the present disclosure includes a plurality of sensors 280, e.g., a current sensor 280a, a voltage sensor 280b, or a power sensor (not shown). The plurality of sensors are designed with sufficient bandwidth to accurately measure across the wide range of frequencies which the amplifier 228 can operate. Various components of the generator 200, namely, the amplifier 228, the current and voltage sensors 280a and 280b, may be disposed on a printed circuit board (PCB). The current sensor 280a is coupled to the active terminal 230 and provides measurements of the current supplied by the amplifier 228. The voltage sensor 280b is coupled to the active and return terminals 230 and 232 provides measurements of the voltage supplied by the amplifier 228. In embodiments, the current and voltage sensors 280a and 280b may be coupled to active and return leads 228a and 228b, which interconnect the active and return terminals 230 and 232 to the amplifier 228, respectively.

The current and voltage sensors 280a and 280b provide the sensed voltage and current signals, respectively, to the controller 224, which then may adjust output of the power supply 227 and/or the amplifier 228 in response to the sensed voltage and current signals. The controller 224 also receives input signals from the input controls of the generator 200, the electrosurgical instrument 20, electrosurgical forceps 30, and/or ultrasonic surgical instrument 40, including, for example, a desired displacement 308 of the ultrasonic surgical instrument 40. The controller 224 utilizes the input signals to adjust power outputted by the generator 200 and/or performs other control functions thereon.

Figure 4:
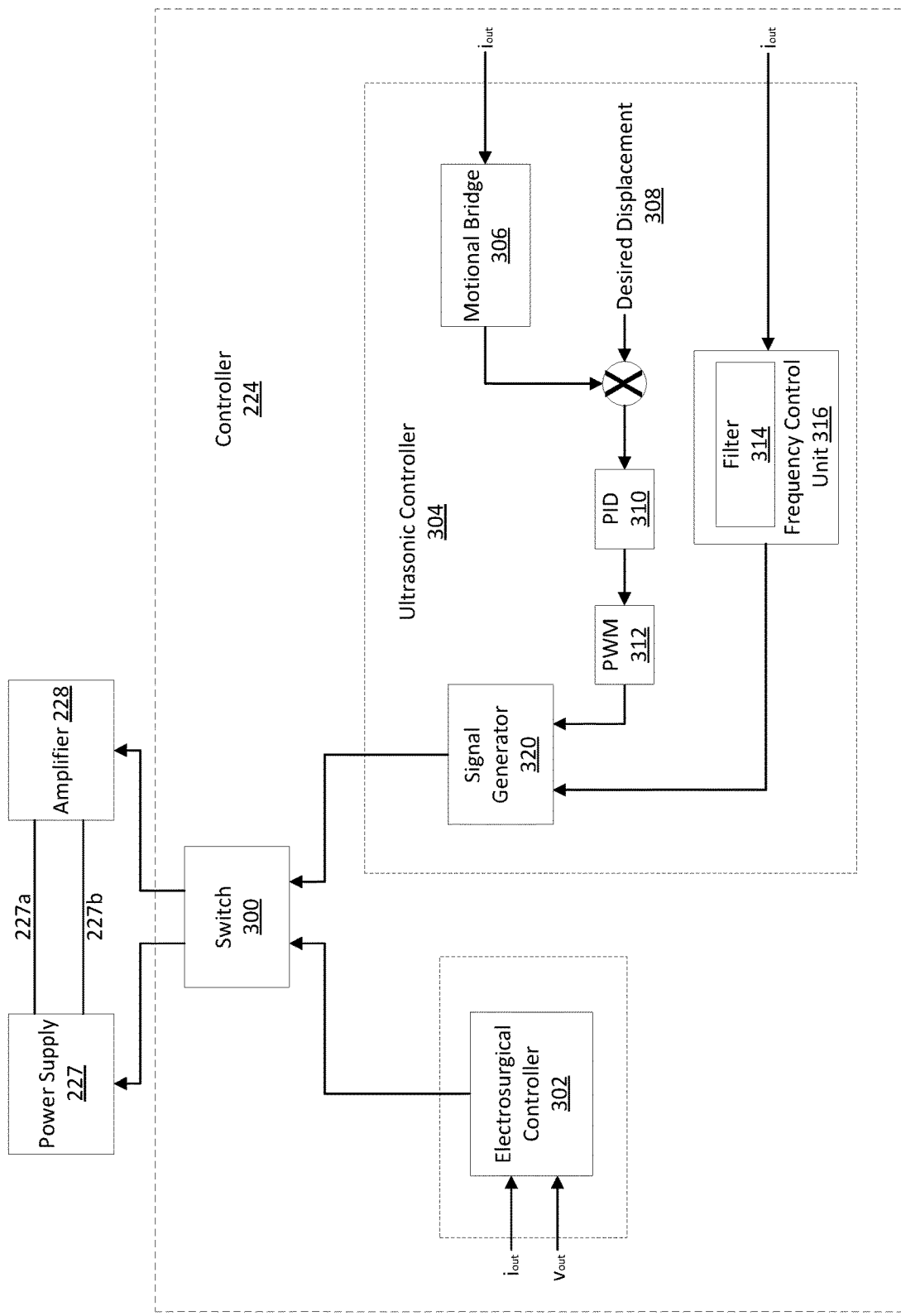
FIG. 4 is a schematic, block diagram of the controller of the generator of FIG. 2.

With reference to FIG. 4, the controller 224 of generator 200 includes two control sections, namely, an electrosurgical controller 302 and an ultrasonic controller 304. The control signals output by both the electrosurgical controller 302 and an ultrasonic controller 304 pass through a switch 300 prior to signaling the power supply 227 and/or amplifier 228. The switch 300 controls which control signal (i.e., electrosurgical control signals or ultrasonic control signals) to pass to control the amplifier 228 and/or power supply 227. Control signals may be pulse width modulated signals as described in further detail below. The switch 300 can either be manually set by a user by selecting a desired output on the user interface 241 of the generator 200, or automatically by the controller 224, which may be based on a type of instrument being coupled to the generator 200. In embodiments, if the ultrasonic instrument 40 is coupled to port 260, the switch 300 is activated to pass ultrasonic control signals from the ultrasonic controller 304. Alternatively, if a monopolar electrosurgical instrument 20 or electrosurgical forceps 30 are coupled to ports 256 and 258, respectively, switch 300 is activated to pass electrosurgical control signals from electrosurgical controller 302.

The electrosurgical controller 302 is configured to control the amplifier 228 to output an electrosurgical RF waveform in at least one of constant current, constant voltage, or constant power modes. In particular, the electrosurgical controller 302 compares the output voltage "$v_{out}$" and the output current "$i_{out}$" to determine the desired operation of the generator 200 (e.g., constant current, constant voltage, or constant power). The mode selection is generally based on the impedance associated with the tissue being cut. Different types of tissue, such as muscle and fat, have different impedances. In terms of electrosurgical operations, constant power output tends to uniformly vaporize tissue, resulting in clean dissection. Whereas constant voltage output tends to explosively vaporize or carbonize tissue ("black coagulation"), and constant current output tends to thermally coagulate tissue without vaporization ("white coagulation"). Carbonization is surgically useful if the surgeon wishes to rapidly destroy surface tissue, and thermal coagulation is regularly coupled with mechanical pressure to seal hepatic or lymphatic vessels shut. However, the surgeon generally desires to operate using constant power output and return to using constant power output as quickly as possible if there is deviation.

Similar to the electrosurgical controller 302, the ultrasonic controller 304 also receives measured output current "$i_{out}$" at the active terminal 230 and return terminal 232. However, the components of the ultrasonic controller 302 portion of the controller 224 differ. The ultrasonic controller 304 includes a motional bridge 306, a proportional-integral-derivative ("PID") controller 310, a pulse-width modulator ("PWM") 312, a frequency control unit 316 and a filter 314. Unlike electrosurgical generators, which run at a fixed frequency defined by a system clock and where the exact frequency is not of particular importance, ultrasonic devices may include a control mechanism to precisely track the resonant frequency of the transducer 44 down to single-digit-Hertz and to adjust the operating frequency of the generator to match the resonant frequency. The motional bridge 306 measures the mechanical motion of the ultrasonic transducer 44 and provides a motional feedback signal representing the mechanical motion of the ultrasonic transducer 44. In particular, the motional bridge 306 produces a feedback signal in proportion to and in phase with the mechanical motion of the transducer 44 and waveguide 46. The output signal of the motional bridge 306 is compared with a desired displacement 308 of the mechanical motion of the ultrasonic transducer 44. The desired displacement 308 may be determined automatically based on the desired output frequency of the ultrasonic surgical instrument 40 or can be set manually by a user, for example, by selecting a HI/LOW switch/button (not shown) on the user interface 241 of the generator 200 or on the ultrasonic surgical instrument 40. The combined signal from the desired displacement 308 and the motional bridge 306 is received by the PID controller 310. The PID controller 310 performs frequency-shifting of the output signal to generate a corrected control signal based on a comparison of the motional feedback signal generated by the motional bridge 306 and the desired displacement 308. The PWM 312 controls the frequency of the output waveform and maintains a constant ultrasonic amplitude of the control signal through modulation of the duty cycle.

In addition to error correction by the PID controller 310, a frequency control unit 316 adjusts the frequency of the control signal to remain at the resonant frequency of the ultrasonic instrument 40. The frequency control unit 316 further comprises a filter 314 configured to filter out unwanted frequencies. In particular, filter 314 may comprise a high pass and/or low pass filter. The modulated control signals from the PWM 312 and frequency control unit 316 are received by the signal generator 320 to generate an ultrasonic control signal.

The switch 300 receives the electrosurgical control signal from the electrosurgical controller 302 and/or the ultrasonic control signal from the ultrasonic controller 304. Depending on the type of the instrument coupled to the generator 200, the amplifier 228 and/or power supply 227 receives either the electrosurgical control signal or the ultrasonic control signal from the switch 300.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical generator, comprising:
   a power supply;
   an amplifier coupled to the power supply and configured to output a first waveform and a second waveform;
   a first controller having a first processor configured to provide a first control signal for generating the first waveform;
   a second controller having a second processor configured to provide a second control signal for generating the second waveform; and a switch configured to receive the first control signal and the second control signal, and to pass through one of the first control signal or the second control signal to at least one of the power supply or the amplifier.

2. The surgical generator according to claim 1, wherein the first controller is an electrosurgical controller and the first control signal is a radiofrequency (RF) control signal.

3. The surgical generator according to claim 1, wherein the second controller is an ultrasonic controller and the second control signal is an ultrasonic control signal.

4. The surgical generator according to claim 3, wherein the ultrasonic controller includes:
   a motional bridge configured to receive an output current of the amplifier and generate a motional feedback signal in proportion to and in phase with a mechanical motion of an ultrasonic transducer;
   a proportional-integral-derivative controller configured to correct the motional feedback signal based on a comparison of the motional feedback signal and a desired displacement of the ultrasonic transducer;
   a pulse-width modulator configured to modulate the motional feedback signal;
   a frequency control unit configured to receive the output current of the amplifier and generate a frequency control signal based on a comparison of a frequency of the second waveform and a resonant frequency of the ultrasonic transducer; and
   a signal generator configured to generate the ultrasonic control signal based on the motional feedback signal and the frequency control signal.

5. The surgical generator according to claim 1, wherein the amplifier is a non-resonant amplifier.

6. The surgical generator according to claim 1, wherein the amplifier is coupled to an active terminal and a return terminal.

7. The surgical generator according to claim 6, wherein the active terminal and return terminal are coupled to a plurality of ports.

8. The surgical generator according to claim 7, further comprising a hub, wherein the hub is coupled to the active and return terminals and the plurality of ports, wherein the hub selectively couples each of the plurality of ports to the active terminal and return terminal.

9. The surgical generator according to claim 1, further comprising at least one of a current sensor, a voltage sensor, and a power sensor.

10. A surgical system, comprising:
    a surgical generator including:
       a power supply;
       an amplifier coupled to the power supply and configured to output a first waveform and a second waveform;
       a first controller having a first processor configured to provide a first control signal for generating the first waveform;
       a second controller having a second processor configured to provide a second control signal for generating the second waveform;
       a switch configured to receive the first control signal and the second control signal and to pass through one of the first control signal or the second control signal to at least one of the power supply or the amplifier;
       a first output outputting the first waveform controlled by the first control signal; and
       a second output outputting the second waveform controlled by the second control signal;
    a first instrument coupled to the first output and energizable by the first waveform; and
    a second instrument coupled to the second output and energizable by the second waveform.

11. The surgical system according to claim 10, wherein the first instrument is an ultrasonic instrument including a transducer energizable by the first waveform.

12. The surgical system according to claim 10, wherein the first instrument is a first electrosurgical instrument including at least one first electrode configured to contact tissue and transmit the first waveform thereto.

13. The surgical system according to claim 10, wherein the second instrument is an electrosurgical instrument including at least one second electrode configured to contact tissue and transmit the second waveform thereto.

14. The surgical system according to claim 10, wherein the first controller is an electrosurgical controller and the first control signal is a radiofrequency (RF) control signal.

15. The surgical system according to claim 10, wherein the second controller is an ultrasonic controller and the second control signal is an ultrasonic control signal.

16. The surgical system according to claim 15, wherein the ultrasonic controller includes:
    a motional bridge configured to receive an output current of the amplifier and generate a motional feedback signal in proportion to and in phase with a mechanical motion of an ultrasonic transducer;
    a proportional-integral-derivative controller configured to correct the motional feedback signal based on a comparison of the motional feedback signal and a desired displacement of the ultrasonic transducer;
    a pulse-width modulator configured to modulate the motional feedback signal;
    a frequency control unit configured to receive an output current of the amplifier and generate a frequency control signal based on a comparison of a frequency of the second waveform and a resonant frequency of the ultrasonic transducer; and
    a signal generator configured to generate the ultrasonic control signal based on the motional feedback signal and the frequency control signal.

17. The surgical system according to claim 10, wherein the amplifier is a non-resonant amplifier.

18. The surgical system according to claim 10, wherein the amplifier is coupled to an active terminal and a return terminal, wherein the active terminal and return terminal are coupled to the first output and the second output.

* * * * *